United States Patent [19]
Higley

[11] Patent Number: 5,356,375
[45] Date of Patent: Oct. 18, 1994

[54] POSITIVE PRESSURE FLUID DELIVERY AND WASTE REMOVAL SYSTEM

[75] Inventor: Robert E. Higley, Queensbury, N.Y.

[73] Assignee: Namic U.S.A. Corporation, Glens Falls, N.Y.

[21] Appl. No.: 863,999

[22] Filed: Apr. 6, 1992

[51] Int. Cl.$^5$ .............................................. A61M 1/00
[52] U.S. Cl. ...................................... 604/30; 604/35; 604/80; 604/142; 604/247
[58] Field of Search ................... 604/30, 80, 82–83, 604/132, 142, 246–247, 35, 73, 118, 122, 124, 27

[56] References Cited

U.S. PATENT DOCUMENTS

| | | | |
|---|---|---|---|
| 2,954,028 | 9/1960 | Smith | 604/80 |
| 3,153,414 | 10/1964 | Beall et al. | 604/142 X |
| 3,429,313 | 2/1969 | Romanelli | 604/35 X |
| 4,084,606 | 4/1978 | Mittleman | 137/102 |
| 4,246,932 | 1/1981 | Raines | 137/512 |
| 4,795,441 | 1/1989 | Bhatt | 604/124 |
| 4,908,018 | 3/1990 | Thomsen | 604/83 |
| 4,915,688 | 4/1990 | Bischof et al. | 604/83 |
| 5,002,528 | 3/1991 | Palestrant | 604/28 |
| 5,127,904 | 7/1992 | Loo et al. | 604/83 |

OTHER PUBLICATIONS

NAMIC® "SOSA™ Pressurized Contrast Delivery System" brochure dated Jul. 1991.
NAMIC® "MORSE® Manifold" brochure dated Jul. 1990.
NAMIC® "ANGIO-SAC®" brochure dated Sep. 1988.

Primary Examiner—C. Fred Rosenbaum
Assistant Examiner—Corrine Maglione
Attorney, Agent, or Firm—Kenyon & Kenyon

[57] ABSTRACT

A pressurized intravenous fluid delivery apparatus that operates as a closed system incorporating a waste component to avoid the accidental injection of air. The apparatus comprises a fluid reservoir under pressure, a manifold with a series of stopcock, an exhaust means in fluid connection with both the fluid reservoir and the manifold by means of a dual check valve, and a cannula and syringe means for injecting fluid into a patient. The closed system facilitates the flushing of blood and air out a catheter without the necessity of disconnecting any part of the apparatus and thereby risking exposure to air or risking physician contact with body fluids. The system is useful for delivering any quantity of one or more fluids under pressure, while avoiding the injection of air.

20 Claims, 7 Drawing Sheets

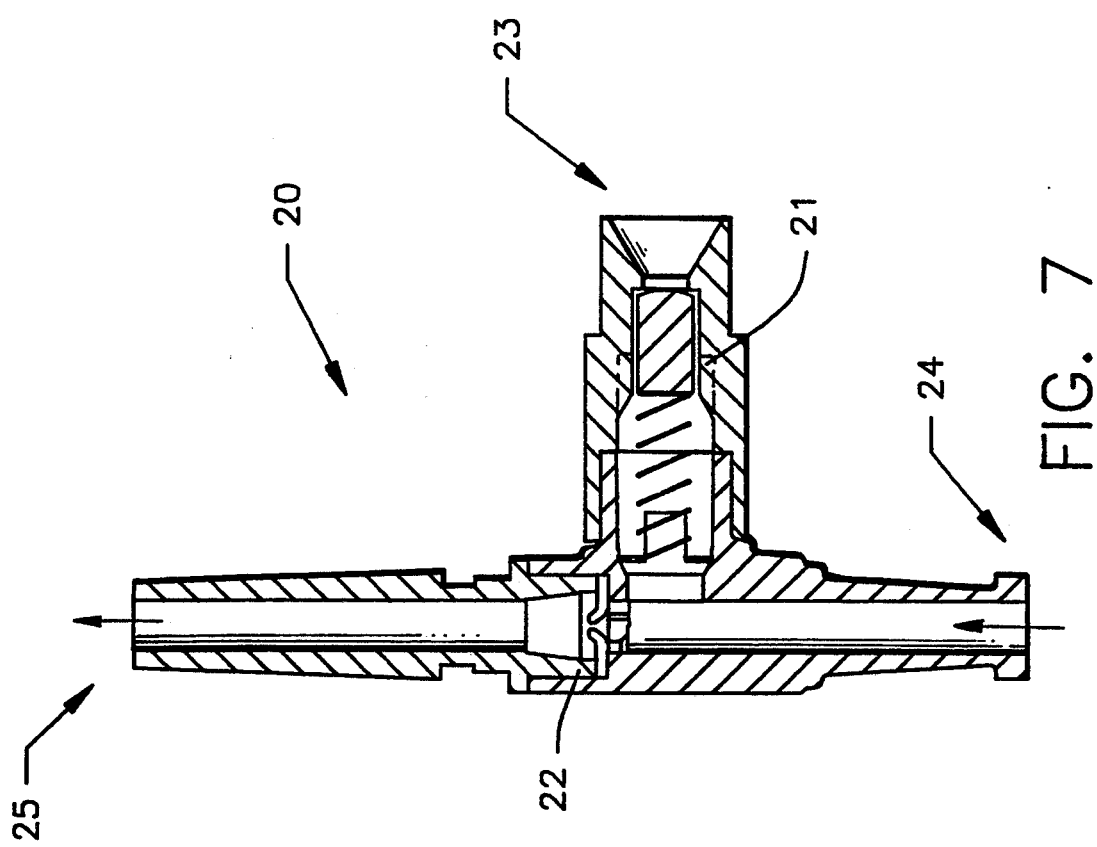
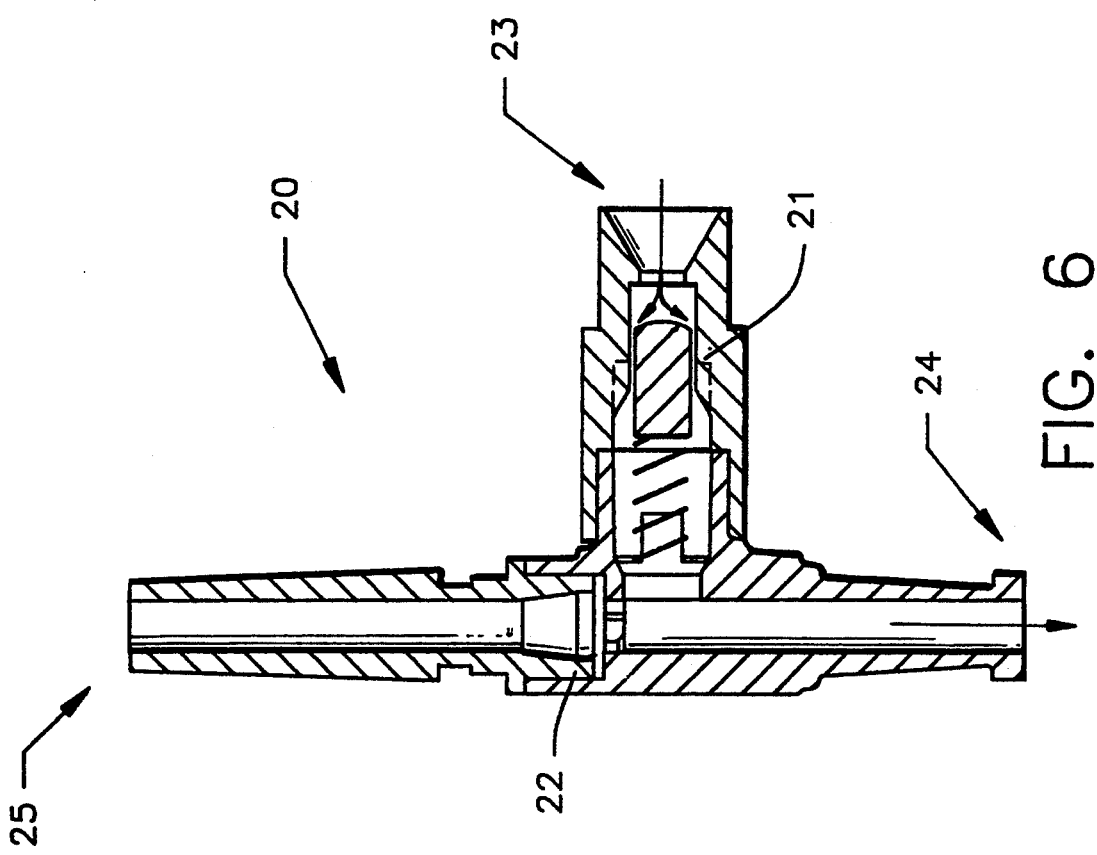

POSITIVE PRESSURE FLUID DELIVERY AND WASTE REMOVAL SYSTEM

BACKGROUND OF THE INVENTION a. Field of the Invention

This invention relates to a fluid delivery apparatus for use in a medical setting which operates as a closed pressurized system incorporating a dual check valve and waste container and which facilitates positive flow delivery of fluids to a patient while helping prevent the accidental injection of air.

b. Description of the Prior Art

In the medical setting, and primarily in angiography, avoiding the accidental injection of air into a patient's vascular system is of great importance. The injection of an air bubble into a vein or artery while administering fluid can result in severe medical complications and even death.

Prior art fluid delivery systems that aspirate fluid from a reservoir by vacuum increase the risk for accidental injection of air into a patient because as fluid is vacuum drawn for subsequent injection into a patient, there is a risk that, in addition to the fluid, gas from suspension in the fluid can be drawn. This drawn gas can be introduced into the vascular system with the fluid upon injection.

Pressurized systems aid in avoiding the accidental injection of air associated with vacuum aspirated systems. With a pressurized system, fluid is forced under pressure into the syringe of the fluid delivery apparatus, and the potential for drawing gas from suspension is eliminated. However, the potential for injection of contaminants and gases may still exist with a pressurized system unless that system remains closed at all times during a fluid delivery procedure. A risk that air could accidently enter the system and be directed toward the patient is presented each time some part of the system is opened.

Pressurized fluid delivery systems are useful for delivering saline and contrast media in cardiac catheterization procedures. Although, ideally, such fluid delivery systems should remain closed, typical prior art pressurized systems are opened during normal use. In catheterization procedures a catheter is aspirated and flushed after it has been inserted into a patient. This involves the aspiration of blood from the patient. Aspirated blood and air must be discarded prior to the introduction of saline and contrast media. In systems without a waste component, the apparatus needs to be disconnected to eliminate this waste. In so doing, the system is opened to the environment, risking both the further introduction of air or other contaminants as well as physician contact with body fluids.

It may be desirable to view several locations in a patient's vascular system during a single catheterization procedure. This may require the use of different specially designed catheters to facilitate access to each location within the vascular system. Thus, catheters will be disconnected and replaced during a single procedure. Each time a new catheter is inserted, it must be connected to the fluid delivery apparatus, aspirated and flushed. The aspirated blood and air need to be discarded each time. Without a waste component in the system, the apparatus is disconnected to externally dispel waste. The risk of the introduction of air therefore may be increased with modern cardiac catheterization procedures, for example, because the need and practice of using different catheters during a single procedure causes the system to be repeatedly opened to the environment.

OBJECTIVES AND SUMMARY OF THE INVENTION

In view of the shortcomings of the prior art, it is an object of the present invention to provide a system for fluid delivery which reduces the risk of accidental injection of air.

It is another object of the present invention to provide a fluid delivery system which safely facilitates positive fluid flow.

It is a further object of the present invention to provide a closed pressurized system for the delivery of contrast media or other fluids to a patient that remains closed while different catheters are disconnected and reconnected, thus avoiding the introduction of air or other contaminants into the system and limiting physician contact with body fluids during the procedure.

It is a further object of the present invention to provide for a method of use of a closed pressurized fluid delivery system which avoids the accidental injection of air.

Other objectives and advantages will become apparent from the following description. Briefly, the present invention provides an apparatus for supplying an intravenous fluid to a patient, comprising: a first fluid reservoir; a manifold; a first tubing means connecting said first fluid reservoir and said manifold for allowing fluid flow from said first fluid reservoir to said manifold; means for pressurizing said first fluid reservoir to enhance fluid flow from said first fluid reservoir to said manifold; a waste container in fluid connection with said manifold; a dual check valve disposed between said first tubing means and said manifold and between said waste container and said manifold comprising, an intake check valve allowing one-directional fluid flow from said first fluid reservoir to said manifold, and an exhaust check valve allowing one-directional fluid flow from said manifold to said waste container; cannula means connected to said manifold for the delivery of intravenous fluid to a patient; and syringe means connected to said manifold for injecting fluid from said manifold into said cannula and for injecting fluid from said manifold into said waste container.

The apparatus can also accommodate a second fluid reservoir component connected to the manifold for delivering fluid under pressure to the manifold.

BRIEF DESCRIPTION OF THE DRAWINGS

FIG. 6 shows a dual check valve with a spring piston intake check valve and its function during aspiration.

FIG. 7 shows a dual check valve with a spring piston intake check valve and its function during injection.

DETAILED DESCRIPTION OF THE INVENTION

Figure 1:
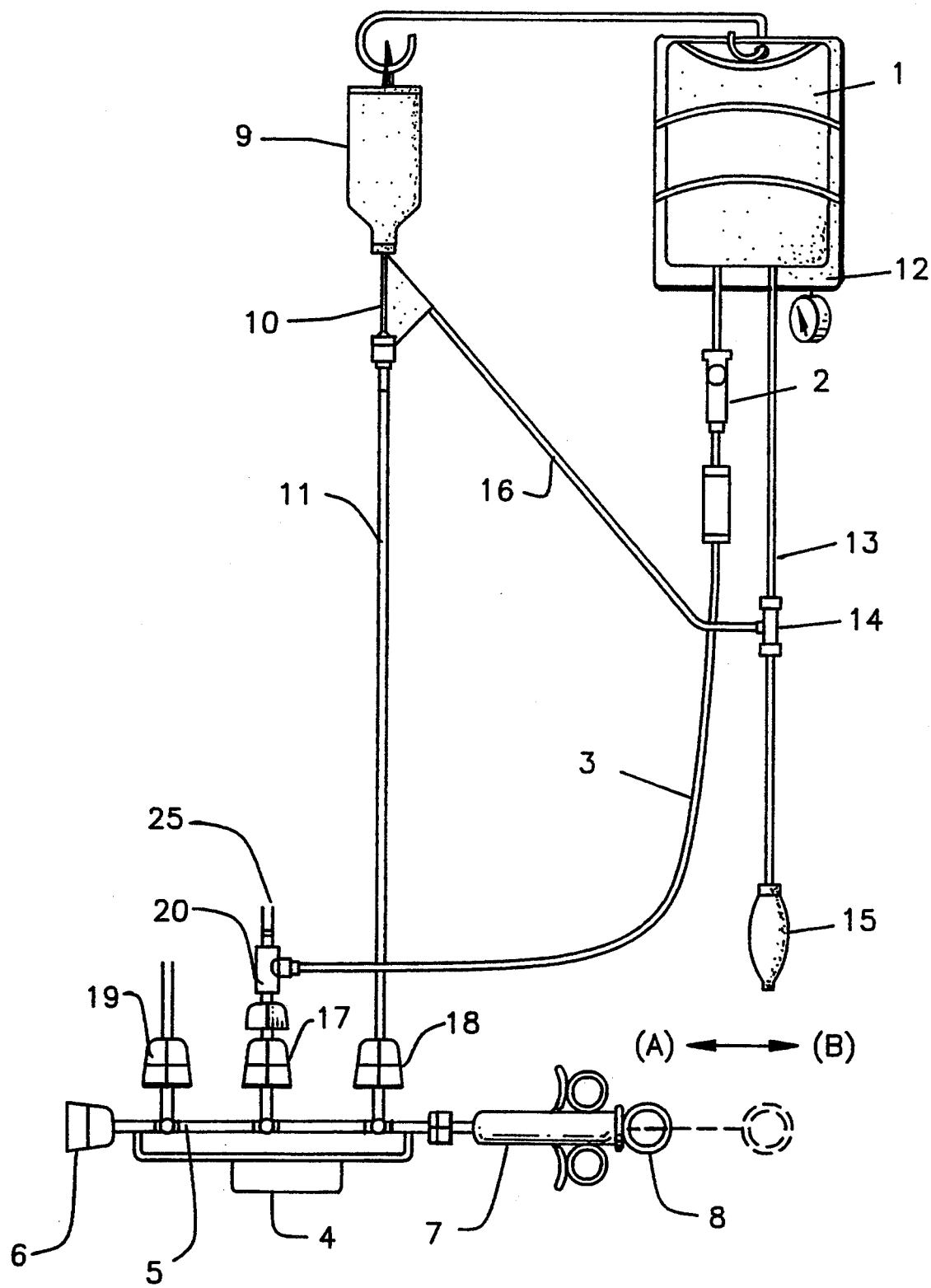
FIG. 1 shows a pressurized dual fluid delivery system containing a dual check valve and waste means constructed in accordance with this invention.

A pressurized fluid delivery system constructed in accordance with this invention may include two component branches, a first component branch and a second component branch. With reference to FIG. 1, the first component branch comprises a first fluid reservoir 1 housing fluid under pressure. A non-vented fluid spike 2 connects the first fluid reservoir 1 to a first tubing 3. Large bore tubing is preferred. The first tubing 3 connects the first fluid reservoir 1 to a manifold 4. Fluid in this first component branch moves from the first fluid reservoir 1 through the first tubing 3 to the manifold 4 with a main lumen 5 where it may be delivered to a patient through a catheter (not shown) connected to the manifold at a catheter connection point 6. A syringe 7 with plunger 8 connects to the manifold 4 and fills with fluid from the manifold 4 for injection to the patient. The first component branch can be used to house and deliver saline.

A second component branch may also be connected to the manifold 4 which may be used to contain and deliver contrast media for cardiac catheterization imaging. The second component branch includes a second fluid reservoir 9. A glass reservoir is presently preferred because it provides a non-reactive housing useful for contrast media. Contrast media used in cardiac imaging procedures has a deleterious effect on most plastics. A fluid spike 10 connects the second fluid reservoir 9 to a second tubing 11. A two-way fluid spike with an air filter is preferred for use with a pressurized second component branch. Large bore tubing is preferred. Fluid flows from the second fluid reservoir 9 through the second tubing 11 to the manifold 4 where it can be directed to the patient through the catheter (not shown) connected at point 6 by means of injection by the syringe 7 with plunger 8.

The system can be pressurized as follows. In the first component branch, the first fluid reservoir 1 may be a compliant bag which can be inserted into a pressure infuser bag 12. A squeeze bulb 15 is connected by a third tubing means 13 to the pressure infuser bag 12 in the first component branch and by a "T" fitting 14 and connecting tube 16 to the two-way fluid spike 10 in the second component branch. This configuration allows the pressure infuser bag 12 to be pressurized thereby compressing the first fluid reservoir 1.

Conversely, the pressure infuser bag 12 also generates compressed air for delivery to the second component branch through the "T" fitting 14 and connecting tube 16. This compressed air is filtered of dust and bacteria in the two-way fluid spike 10 and pressurizes the second fluid reservoir 9 of the second component branch. A two-way fluid spike with a 0.2 micron air filter is preferred. Both the fluid of the first component branch such as saline and the fluid of the second branch such as contrast media flow toward the manifold 4 under pressure.

Although this fluid delivery system is useful for the delivery of contrast media for imaging procedures in angiography, such use does not limit the scope of this invention. This system can be used for the delivery of any combination of different components where it is necessary or desirable to maintain a closed system and limit the risk of accidental delivery of air or other contaminants.

A preferred embodiment of this fluid delivery system is intended to operate as a closed system once the apparatus is connected to a catheter that has been inserted into the patient. The system remains closed by using a manifold with connecting side ports that can be turned on and off in order that flow be directed appropriately and that the system be self contained. A MORSE® manifold available from NAMIC U.S.A. Corporation, Glens Falls, N.Y., is preferred.

A preferred manifold 4 is equipped with side ports for connection to the component branches which can be opened and closed to facilitate or prevent fluid flow. At a first port 17, the first component branch of the system is connected to the manifold 4. The first tubing 3 of the first component branch connects to the manifold 4 by means of a dual check valve 20. The structure and function of this dual check valve is described in detail below. Saline, for example, can be delivered from the first component branch to the manifold 4 through the first port 17. At a second port 18, the second component branch is connected by the second tubing 11 to the manifold 4. Contrast media, for example can be delivered to the manifold through this second port 18. A third port 19 can be used as an outlet to a transducer (not shown) such that pressure can be measured and monitored.

The syringe 7 is filled with saline or contrast media by opening select side ports 17 or 18 of the manifold 4 and pressurizing the system with the pressure infuser bag 12. Fluid flows into the manifold 4 under pressure from either the first component branch or the second component branch. Fluid fills the manifold 4 and syringe 7, forcing the plunger 8 in the syringe 7 from position A to position B. When the syringe 7 is filled with fluid, the ports 17 and 18 can be turned "off". This closes the fluid path from the reservoirs to the manifold 4 and opens the path through a main lumen 5 of the manifold 4 from the syringe 7 to the catheter (not shown) connected at point 6. Fluid can be expelled from the manifold 4 to the catheter for injection into a patient by pushing the syringe plunger 8 from position B to position A. Closing the side ports 17 and 18 before injection prevents fluid back-up into the fluid delivery system.

The dual check valve 20 in the first component branch and waste container (not shown) connected at point 25 to the dual check valve 20 allow flushing of blood and air from the system without disconnecting the syringe 7 from the manifold 4. A preferred waste container is the NAMIC® Anglo-Sac ™ available from NAMIC U.S.A. Corporation, Glens Falls, N.Y.

Air is usually present inside a catheter which is inserted into the vascular system of a patient. Prior to fluid delivery, this air must be expelled. After connection of a catheter to the manifold 4 of the pressurized system, blood can be aspirated from the patient by closing the side ports 17, 18 and 19 on the manifold 4 and pulling the plunger 8 of the syringe from position A to position B. This flushes the air out of the catheter, drawing the air and blood into the manifold 4 and syringe 7. To insure that all of the air has been flushed from the catheter, some blood will be drawn into the main lumen 5 of the manifold 4 and possibly into the syringe 7. This blood and air must then be expelled from the system to prevent the introduction of air into the patient's vascular system. Where physicians would disconnect prior art systems to discard waste from the syringe, this invention provides a significant and useful improvement by incorporating the dual check valve 20 and waste container (not shown). In combination, these parts incorporated at a first port 17, where saline may pass, provide means for expelling waste and rinsing the syringe without disconnecting the syringe 7 from the manifold 4. The system remains closed.

Waste may be expelled from the system of the present invention by opening first port 17 while keeping the other side ports 18 and 19 closed. Opening the first port 17 closes the path between the manifold 4 and the patient and opens the path between the manifold 4 and the dual check valve 20. The syringe plunger 8 is pushed from position B to position A. The air and waste moves through the first port 17 and into the dual check valve 20. With pressure generated by the movement of the syringe plunger 8, rather than from that generated by the pressure infuser bag 12, the valve closes the fluid path to the first component branch and opens the fluid path to the waste container (not shown) connected at point 25. The contents of the syringe 7 empty into the waste container upon pushing the syringe plunger 8 from position B to position A. Fluid from the first fluid reservoir 1 can then be forced into the manifold 4 and empty syringe 7 merely by pressurizing the pressure infuser bag 12. Pressure from this direction causes the dual check valve 20 to open the fluid path from the first fluid reservoir 1 to the manifold 4 while closing the fluid path from the manifold 4 to the waste container.

Figure 2:
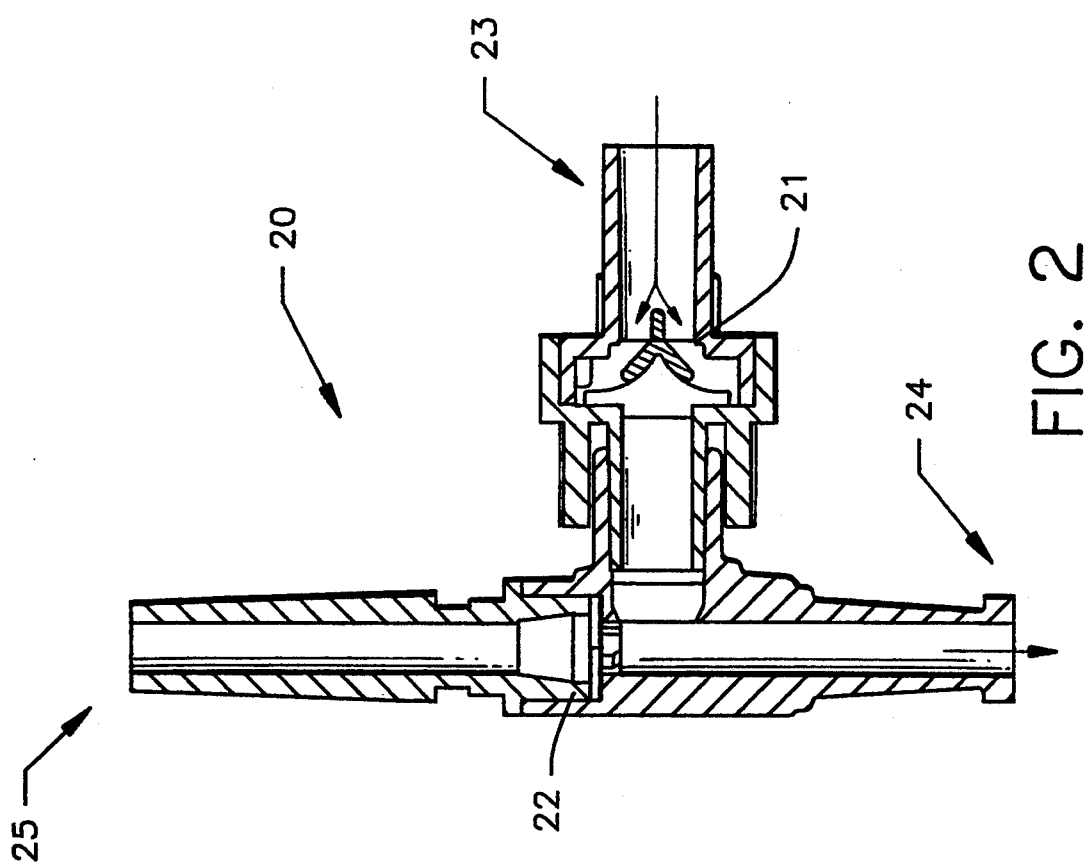
FIG. 2 shows a dual check valve and its function during aspiration.
Figure 3:
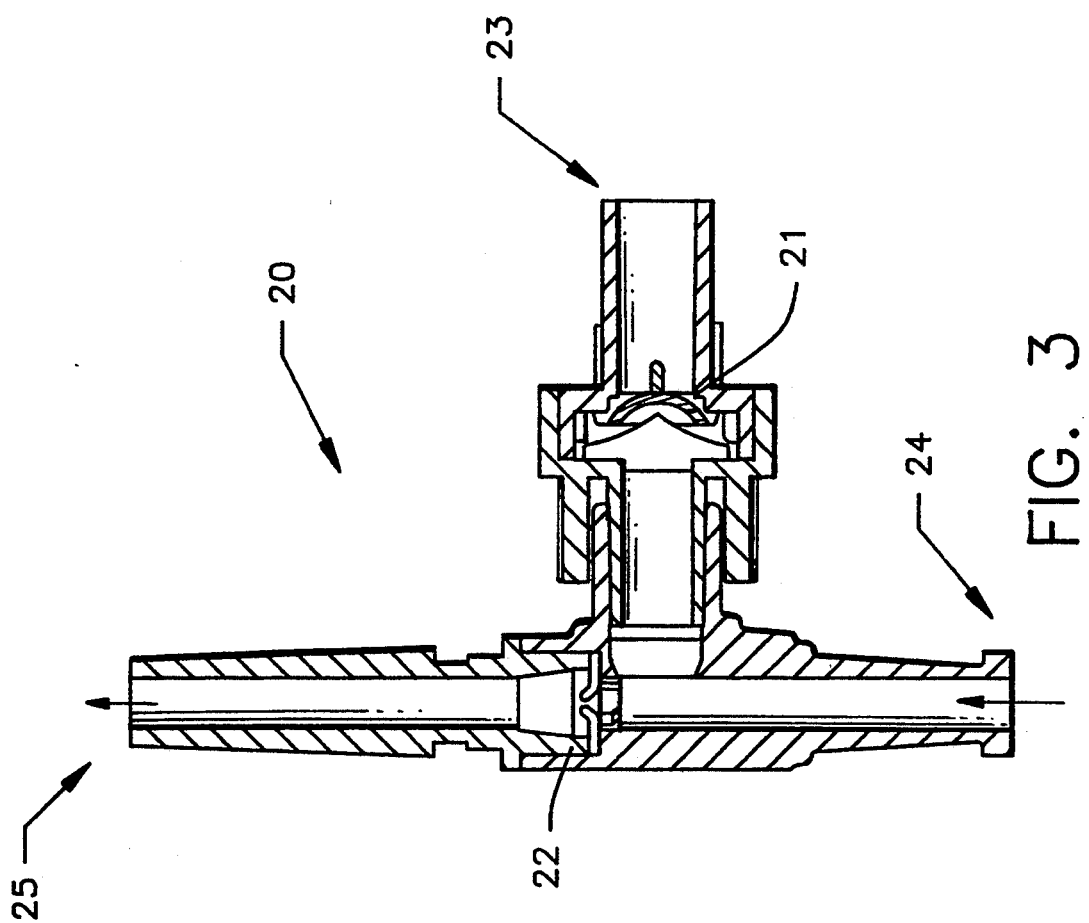
FIG. 3 shows a dual check valve and its function during injection.

FIGS. 2 and 3 show the detail of one type of dual check valve operating in this system. This dual check valve connects to the first tubing 3 at point 23, connects to the manifold 4 at 24, and connects to the waste container at 25. Pressurized fluid from the first component branch flows into the intake check valve 21 as shown in FIG. 2. During aspiration from the first fluid reservoir 1, fluid under positive pressure created by the pressure infuser bag 12 or other pressure generation means opens the intake check valve 21 and moves through the valve to the manifold 4. The intake check valve 21 remains open during aspiration from the first fluid reservoir and closes at the point of equal pressure when the manifold 4 has been filled with fluid. During aspiration from the first fluid reservoir 1 the exhaust check valve 22 remains closed.

In contrast, FIG. 3 shows the operation and fluid path of the dual check valve during disposal of waste. During disposal of waste into the waste container, the syringe plunger 8 is pushed from position B to position A. The exhaust check valve 22 opens and allows fluid to empty into the waste container. The intake check valve 21 now subject to back pressure from the syringe plunger 8 remains closed. The pressure needed to open the fluid path to the waste container is generated by pushing the syringe plunger 8 from position B to position A. The exhaust check valve 22 opens at a critical pressure called the cracking pressure. Fluid flows out through the exhaust check valve 22 into the waste container connected at point 25. Blood and air that have been aspirated from the patient through the catheter can be expelled from the system in this way without disconnecting the syringe 7 from manifold 4.

Figure 4:
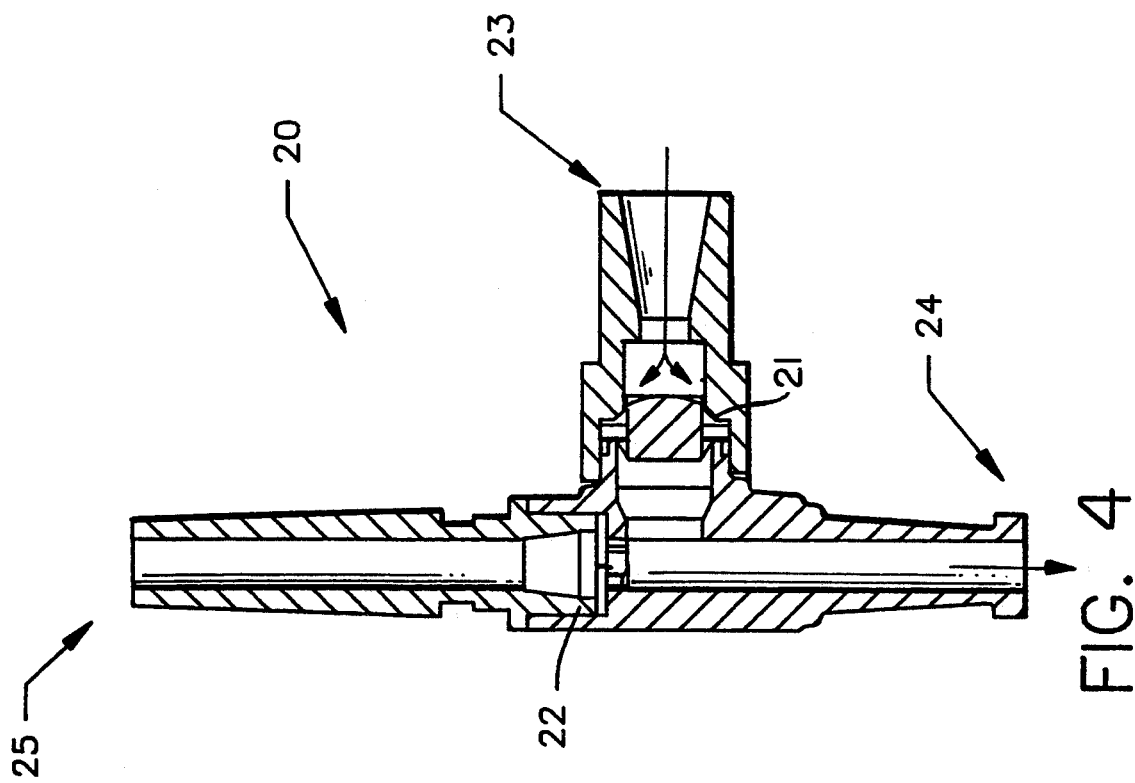
FIG. 4 shows a dual check valve with an elastomeric intake check valve and its function during aspiration.
Figure 5:
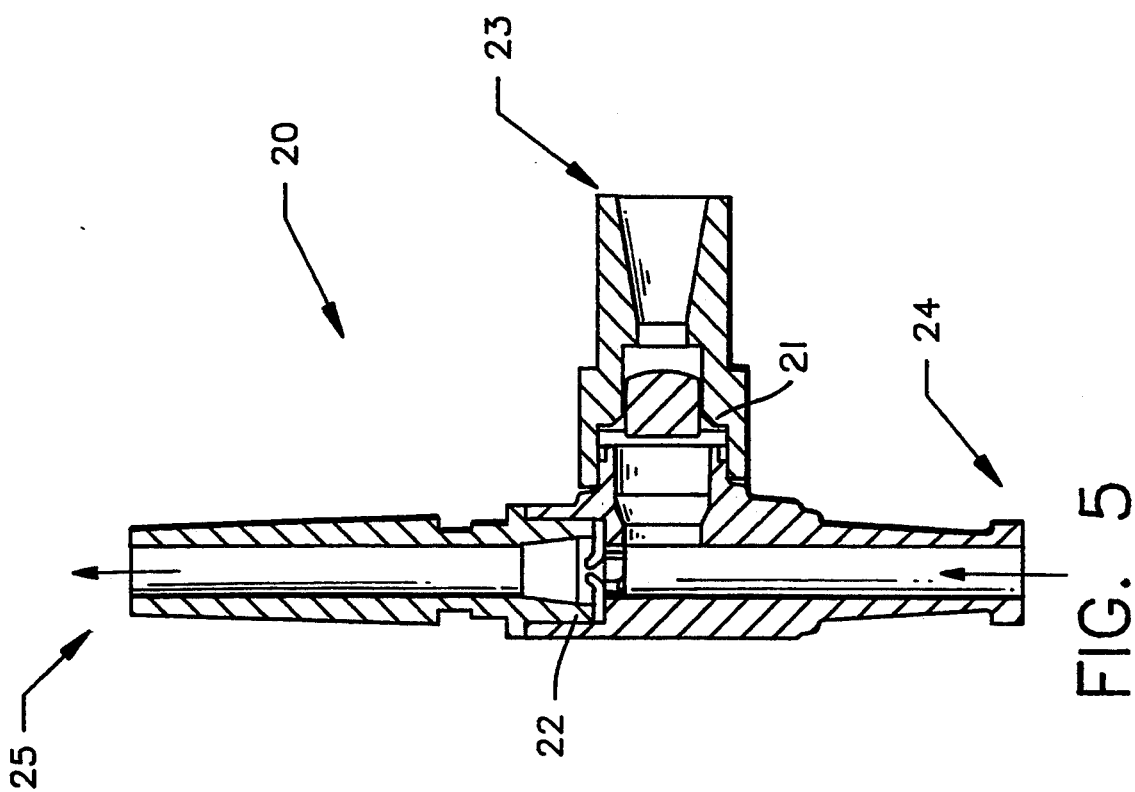
FIG. 5 shows a dual check valve with an elastomeric intake check valve and its function during injection.

The valve shown in FIGS. 2 and 3 is only one type of dual check valve that could be used in this system. This is a NAMIC® hybrid check valve available from NAMIC U.S.A. Corporation, Glens Falls, N.Y. Other preferred check valves appear in FIGS. 4 through 7. FIGS. 4 and 5 show the function of a NAMIC® elastomeric dual check valve during aspiration from the first fluid reservoir 1 and during injection into the waste container at 25, respectively. The intake check valve in FIGS. 4 and 5 is an elastomeric check valve. FIGS. 6 and 7 show the function of a NAMIC® spring piston dual check valve and its function during aspiration and injection, respectively. The intake check valve in FIGS. 6 and 7 is a spring piston type check valve. The valves in FIGS. 4 and 5 and in FIGS. 6 and 7 are available from NAMIC U.S.A. Corporation, Glens Falls, N.Y. Other dual check valves that meet the performance goals of the present invention would also be appropriate.

The first component branch, equipped with the dual check valve and waste container is specifically designed for pressurized systems. The exhaust check valve 22 is designed to withstand the combined resultant pressure of the pressure generation means, the water column, and the negative water column (siphoning effect) of the exhaust system. This exhaust check valve 22 remains closed and the intake check valve 21 remains open when the first fluid reservoir 1 is pressurized to force fluid into the syringe 7. Conversely, when the syringe plunger 8 is pushed in, fluid can be forced out of the exhaust check valve 22 and into the waste container connected at point 25, the intake check valve 21 remaining closed.

A preferable exhaust check valve 22 uses an elastomeric material with a "slit" cut through it. The cracking pressure of the exhaust check valve is determined by material thickness, slit length, and certain elastomeric performance specifications. The thicker the elastomeric material and the smaller the slit, the more resistance the valve presents to the fluid. The thickness, slit length, and elastomeric performance specifications must be specifically balanced to meet the performance goals of the system.

The function of the invention for delivery of cardiac imaging media can be summarized as follows. The apparatus is assembled as illustrated in FIG. 1. The syringe plunger 8 at position A keeps the syringe 7 free of fluid and air. The three manifold side ports 17, 18, and 19 are "off", blocking the path of fluids from the two reservoirs 1 and 9 to the manifold 4 and blocking any signal to the transducer through the third port 19. The first fluid reservoir 1 and the first tubing 3 contain saline which is halted from flow at the first side port 17 on the manifold 5. The second fluid reservoir 9 and the second tubing 11 contain contrast media which is halted from flow into the manifold 4 at the second port 18.

A catheter is inserted into an area within the vascular system of a patient. The catheter is connected to the manifold at 6. This connection forms a closed system between the fluid delivery apparatus and the patient's vascular system. Before the fluid delivery procedure begins, however, the air present in the catheter and in the main lumen 5 of the manifold 4 must be flushed from the system. The air from the catheter is drawn into the syringe 7 by pulling the syringe plunger 8 from position A to position B. Blood is aspirated from the patient into the catheter, moving blood and the column of air into the syringe 7. Blood can be drawn into the apparatus as far back as the syringe 7 to insure that all air has been expelled from the catheter.

With the air and blood in the syringe 7, the first fluid port 17, which had been blocking the saline delivery, is opened. This opens the fluid path between the dual check valve 20 and the manifold 4 and closes the path back to the patient. Saline does not, however, upon opening the first side port 17 in this configuration, flow toward the manifold 4 because of the back pressure caused by the syringe plunger fully extended to position B. Thus, the intake check valve 21 in the dual check valve 20 remains closed and prevents the flow of saline. The syringe plunger 7 can now be pushed from position B to position A. With the first side port 17 opened, the blood, air, and any saline present is forced into the dual check valve 20 rather than toward the patient. The intake check valve 21 remains closed because the pressure from the syringe plunger 8 closes the intake check valve 21, preventing any back-up into the first component branch of the system. The exhaust check valve 22 opens under this pressure created by the plunger 8, and the waste flows into the waste container. These steps can be repeated until all air has been expelled from the system.

It is necessary to prevent blood from sitting motionless in the catheter to reduce the risk of clots forming and being introduced into the patient's vascular system. The catheter may therefor be filled with saline. By pressurizing the pressure infuser bag 12, saline moving under positive pressure from the first reservoir 1, opens the intake check valve 21 and flows into the manifold 4 through the first side port 17. The syringe 7 fills until the syringe plunger 8 is moved from position A to position B. Pushing the plunger 8 again from position B to position A will again open the exhaust check valve 22 and force saline and any blood into the waste container. The intake check valve 21 again remains closed under this pressure from the syringe plunger 8. This procedure of clearing the syringe with saline can be repeated until all of the air and blood have been exhausted from the fluid delivery apparatus.

It is unnecessary to disconnect the syringe from the manifold 4 for purposes of externally dispelling the waste in the system before filling the catheter with saline. The dual check valve 20 in the saline branch of the system also eliminates the need for the practitioner to open separate side ports as both the saline filling the syringe and the waste leaving the syringe move through the first port 17. The dual check valve 20 responds automatically in the appropriate manner to the opposing pressures imposed by the pressure infuser bag 12 upon aspiration from the first fluid reservoir 1 and by the syringe plunger 8 upon pushing from position B to position A to expel waste.

The catheter can be filled with saline by aspirating saline from the first fluid reservoir 1 and then turning the first port 17 "off". This closes the path between the manifold 4 and the dual check valve 20 and opens the path to the patient through the main lumen 5 of the manifold 4. Saline may be forced into the catheter by pushing the syringe plunger 8 from position B to position A.

After all waste has been expelled, the fluid delivery apparatus contains only the fluids to be delivered to the patient from the apparatus, all blood and air having been cleared. The closed system remains closed, and the catheter can be filled with contrast media for delivery to the patient.

Delivery of the contrast media first requires that the syringe 7 be filled by closing the first port 17 and opening the second port 18. Contrast media from the second fluid reservoir 9 fills the syringe 7 and with the third port 19 open, a pressure signal is sent to the transducer (not shown). Once the syringe 7 is filled, the side ports 18 and 19 can be closed. This opens the path through the main lumen 5 of the manifold 4 between the syringe 7 and the patient and closes all paths through the side ports 17, 18, and 19. Contrast media is injected into the patient by pushing the syringe plunger 8 from position B to position A.

This entire procedure can be repeated each time a new catheter needs to be inserted into a new area within the patient's vascular system. The dual check valve 20 and waste container provide the ability to easily flush waste from the system without opening the system to air or risking physician contact with the patient's body fluids.

Figure 8:
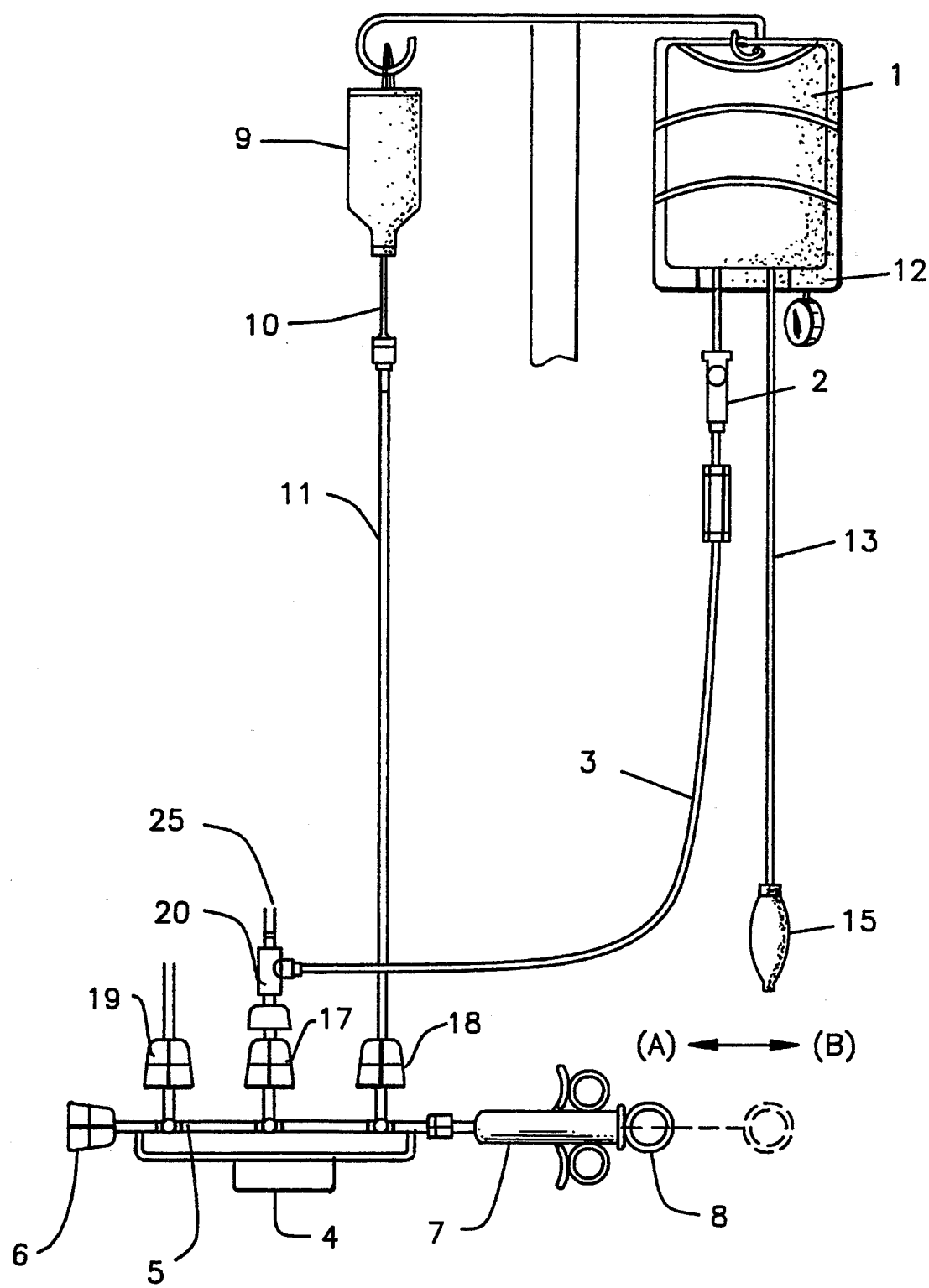
FIG. 8 shows an alternate system similar to FIG. 1 less the means for pressurizing the second fluid reservoir.

Also within the scope of this invention is a pressurized system that omits the second pressurized component branch. Such a system may contain only one component branch which is pressurized and any number of additional non-pressurized component branches. This system is illustrated in FIG. 8. The "T" fitting and tubing connecting the pressure infuser bag configuration to the first component branch as shown in FIG. 1 is omitted from the apparatus in FIG. 8. In the non-pressurized component branch, a vented fluid spike 10 is preferred. It is within the scope of this invention to deliver fluids where only the first component is under pressure and passes through the dual check 20 valve as shown in FIG. 8.

Figure 9:
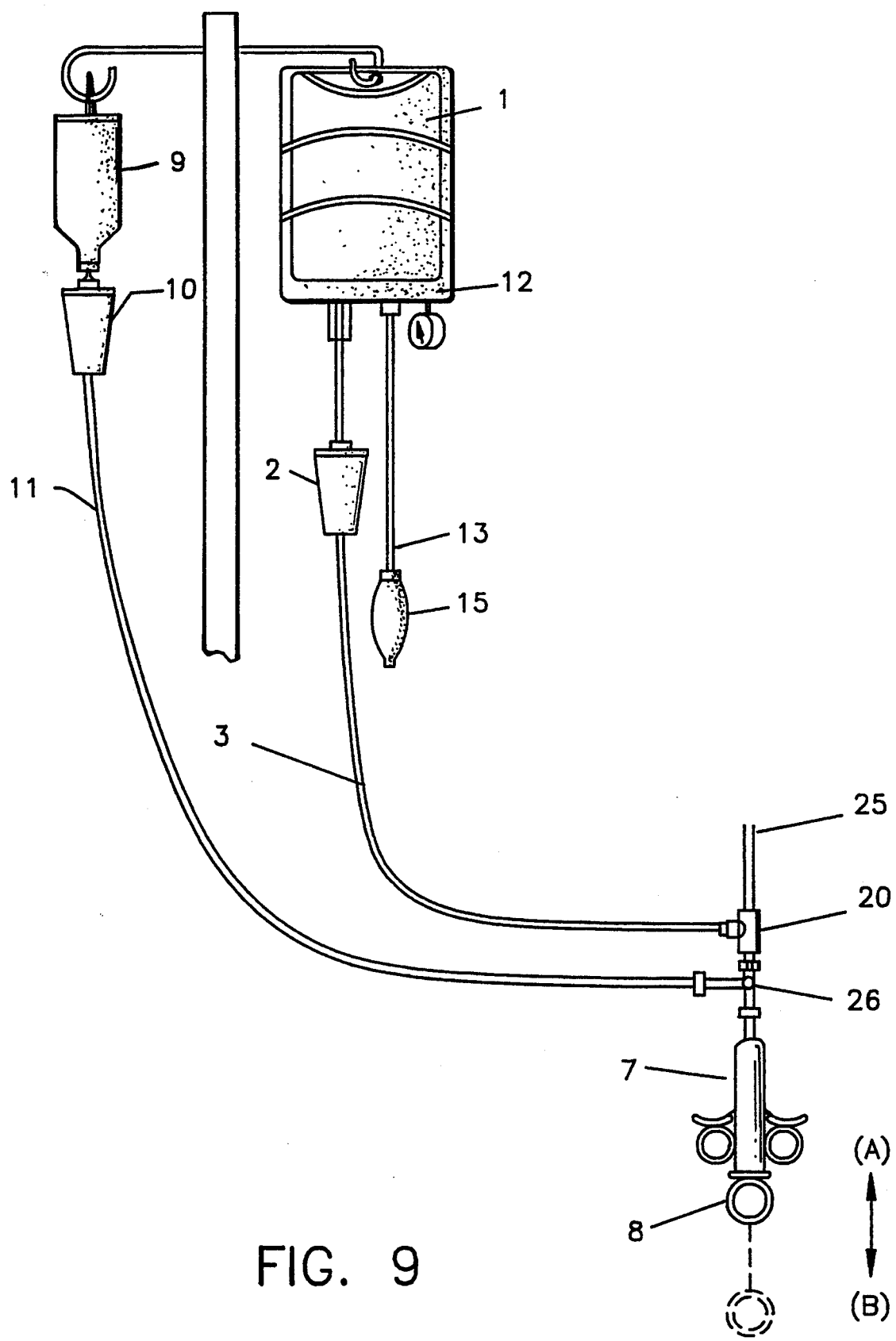
FIG. 9 shows a "backtable" use of a pressurized fluid delivery system containing a dual check valve, waste means, and closable stopcock constructed in accordance with this invention.

An alternate embodiment of this invention involves the "backtable" use of the pressurized system. Such a use may be of value in neuro-radiology or special procedures. FIG. 9 shows an embodiment where the clinical user would connect the syringe to the backtable system, aspirate the desired fluid, disconnect the syringe from the backtable system and reconnect it to the cannula means in the patient. This "backtable" use of the present invention incorporates the waste component and check valve in the first component branch to allow for aspiration from the first fluid reservoir 1 and flushing of waste to the waste container connected at point 25 through the working of the dual check valve 20.

This "backtable" use can encompass either an apparatus where one component branch is pressurized or an apparatus where additional component branches are pressurized, and can be used to deliver fluids such as saline, contrast media or both. FIG. 9 illustrates the "backtable" use where only the first component branch is pressurized.

In FIG. 9, pressurized fluid from the first component branch flows to the dual check valve as discussed in connection with embodiments depicted FIGS. 1 and 8. In contrast, however, the embodiment in FIG. 9 provides for a semi-closed fluid delivery system incorporating an internal waste component. The system is semi-closed, because although the syringe is disconnected from the pressurized system during injection into the patient, it is closed during the disposal of waste.

In order to prevent outflow of fluid from the pressurized system when the syringe is disconnected, a three-way stopcock valve 26 can be incorporated such that the valve can be turned "off" to prevent leakage when the syringe 7 is disconnected. A three-way MORSE® stopcock available from NAMIC U.S.A. Corporation, Glens Falls, N.Y. is preferred for this purpose.

Figure 10:
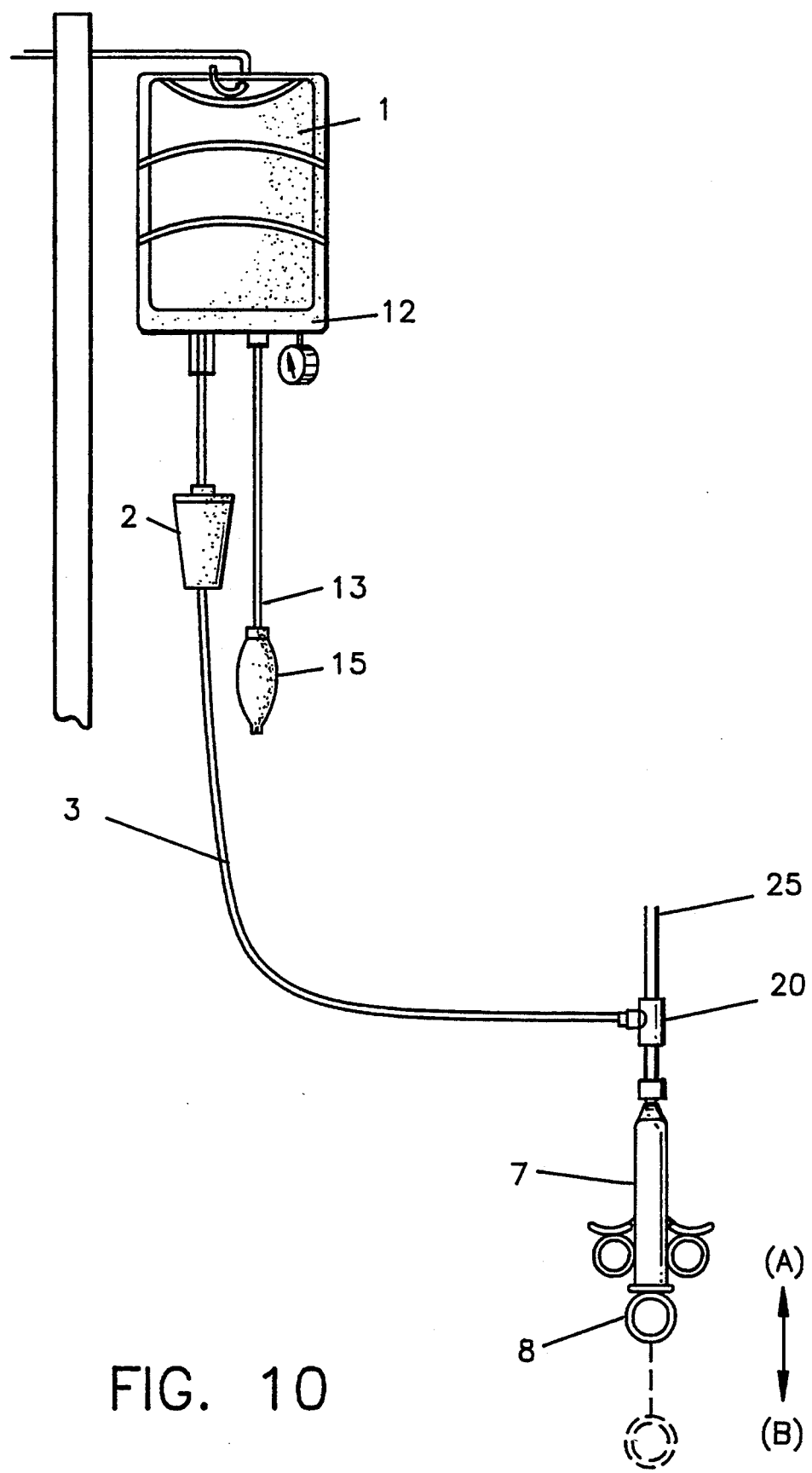
FIG. 10 shows a "backtable" use of a pressurized fluid delivery system containing waste means and a dual check valve with an additional reflux valve constructed in accordance with this invention.

An alternative preferred component to serve a purpose similar to the three-way stopcock valve is a reflux valve which is a normally-closed valve that is opened upon contact with a luer tip such as a syringe tip and closes again upon syringe removal. The incorporation of a reflux valve is illustrated in FIG. 10 where a single pressurized component system is depicted with the reflux valve contained in the dual check valve 20 at the point where the syringe 7 is connected to the dual check valve 20.

In the foregoing specification, the present invention has been described with respect to specific embodiments. These serve as examples to illustrate the invention rather than limit its scope. Modifications may be made without departing from the broader teachings of the invention.

What is claimed is:

1. An improved fluid delivery apparatus having a first fluid reservoir to contain fluid under pressure connected by a first tubing means to a manifold and syringe, wherein the improvement comprises,
   a waste container in fluid connection with the manifold; and
   a dual check valve making a three-way fluid connection between the first tubing means, the manifold and the waste container wherein the dual check valve comprises an intake check valve allowing one-directional fluid flow under positive pressure from the first fluid reservoir to the manifold, and an exhaust check valve allowing one-directional fluid flow under positive pressure from the manifold to the waste container.

2. The fluid delivery apparatus of claim 1 wherein the exhaust check valve of the dual check valve is made from an elastomeric material.

3. The fluid delivery apparatus of claim 2 wherein the exhaust check valve has a slit cut through it.

4. The fluid delivery apparatus of claim 1 wherein the intake check valve is a spring piston check valve.

5. The fluid delivery of claim 1 wherein the intake check valve is an elastomeric check valve.

6. The fluid delivery apparatus of claim 1 wherein the intake check valve is a hybrid check valve.

7. An apparatus for supplying an intravenous fluid to a patient, comprising:
   (a) a first fluid reservoir;
   (b) a manifold;
   (c) a first tubing means connecting said first fluid reservoir to said manifold and allowing fluid flow from said first fluid reservoir to said manifold;
   (d) means for pressurizing said first fluid reservoir to cause fluid to flow from said first fluid reservoir to said manifold;
   (e) a waste container in fluid connection with said manifold;
   (f) a dual check valve disposed between said first tubing means and said manifold and between said waste container and said manifold comprising,
   an intake check valve allowing one-directional fluid flow under positive pressure from said first fluid reservoir to said manifold, and
   an exhaust check valve allowing one-directional fluid flow under positive pressure from said manifold to said waste container;
   (g) a cannula means connected to said manifold for the delivery of intravenous fluid to a patient; and
   (h) means connected to said manifold for injecting fluid from said manifold into said cannula and for injecting fluid from said manifold into said waste container.

8. The apparatus of claim 7 wherein said first fluid reservoir is made of a compliant material.

9. The apparatus of claim 8 wherein said means for pressurizing said first fluid reservoir comprises,
   (a) a pressure infuser bag into which the said first fluid reservoir is inserted,
   (b) an inflation apparatus for forcing air into said pressure infuser bag to compress said first fluid reservoir, and
   (c) a non-vented fluid spike disposed between said first fluid reservoir and said first tubing means.

10. The apparatus of claim 7 wherein said manifold consists of:
    (a) a longitudinal shaft forming a main lumen;
    (b) a first side port, which can be opened and closed, for connection to said dual check valve; and
    (c) a second side port, which can be opened and closed.

11. The apparatus of claim 7 wherein said exhaust check valve in said dual check valve is made from an elastomeric material.

12. The apparatus of claim 11 wherein said exhaust check valve contains a slit cut through it.

13. The apparatus of claim 7 further comprising:
    (i) a second fluid reservoir;
    (j) a second tubing means connecting said second fluid reservoir to said manifold and allowing fluid to flow from said second fluid reservoir to said manifold; and
    (k) means for pressurizing fluid in said second fluid reservoir.

14. The apparatus of claim 13 wherein said second fluid reservoir is made of glass and said first fluid reservoir is made of a compliant material.

15. The apparatus of claim 14 wherein the means for pressurizing fluids in both said first fluid reservoir and said second fluid reservoir comprises:
    (a) a pressure infuser bag, into which said first fluid reservoir is inserted;
    (b) a squeeze bulb for the generation of air;
    (c) a third tubing means for the passage of air connecting said squeeze bulb to said pressure infuser bag;
    (d) a "T" fitting in said third tubing means;
    (e) a two-way fluid spike disposed between said second fluid reservoir and said second tubing means; and
    (f) a fourth tubing means for the passage of air connecting said third tubing means at said "T" fitting to said two-way fluid spike.

16. The apparatus of claim 15 wherein said two-way fluid spike contains a 0.2 micron air filter.

17. The apparatus of claim 13 wherein said manifold consists of:
    (a) a longitudinal shaft with a main lumen;
    (b) a first side port, which can be opened and closed, for connection with said dual check valve;
    (c) a second side port, which can be opened and closed, for connection with said second tubing means; and
    (d) a third side port, which can be opened and closed.

18. The apparatus of claim 13 wherein said exhaust check valve in said dual check valve is made from an elastomeric material.

19. The apparatus of claim 18 wherein said exhaust check valve in said dual check valve has a slit cut through it.

20. An apparatus for supplying an intravenous fluid to a patient, comprising:
 (a) a compliant first fluid reservoir;
 (b) a manifold comprising:
  a longitudinal shaft with a main lumen open at both ends,
  a first side port for the delivery of said first fluid and for the expelling of exhaust, and
  a second side port;
 (c) a first tubing means allowing fluid flow and connecting said first fluid reservoir to said manifold;
 (d) a waste container in fluid connection with said manifold at said first side port;
 (e) a dual check valve connected to said manifold at said first side port and additionally disposed between said first tubing means and said waste container, comprising:
  an intake check valve allowing one-directional fluid flow from said first fluid reservoir to said manifold, and
  an elastomeric exhaust check valve with a slit cut through it allowing one-directional fluid flow from said manifold to said waste container;
 (f) a pressure infuser bag pressure system comprising:
  a pressure infuser bag into which said compliant first fluid reservoir is inserted,
  a non-vented fluid spike disposed between said first fluid reservoir and said first tubing means,
  a squeeze bulb for the generation of air, and
  a second tubing means for the passage of air, connecting said squeeze bulb to said pressure infuser bag;
 (g) a cannula means connected to said manifold at one end of the main lumen for the injection of fluid to a patient and aspiration of fluid from a patient; and
 (h) a syringe connected at its tip to the main lumen of said manifold at the end opposite the cannula for containing fluid and injecting fluid through said manifold into said cannula and for injecting fluid through said manifold into said waste container.

* * * * *